US006835336B2

(12) United States Patent
Watt

(10) Patent No.: US 6,835,336 B2
(45) Date of Patent: Dec. 28, 2004

(54) METHODS FOR MAKING BIOPOLYMER SPONGE TUBES

(75) Inventor: Paul W. Watt, Steeton (GB)

(73) Assignee: Ethicon, Inc., Somerville, NJ (US)

(*) Notice: Subject to any disclaimer, the term of this patent is extended or adjusted under 35 U.S.C. 154(b) by 424 days.

(21) Appl. No.: 09/887,742

(22) Filed: Jun. 22, 2001

(65) Prior Publication Data

US 2002/0010482 A1 Jan. 24, 2002

Related U.S. Application Data

(62) Division of application No. 09/164,793, filed on Oct. 1, 1998.

(30) Foreign Application Priority Data

Oct. 3, 1997 (GB) ................................. 9721079

(51) Int. Cl.[7] .............................................. B29C 39/36
(52) U.S. Cl. ...................... 264/28; 264/297.8; 264/334
(58) Field of Search ............................. 264/28, 41, 49, 264/101, 102, 299, 334, 297.8; 424/426

(56) References Cited

U.S. PATENT DOCUMENTS

| | | | |
|---|---|---|---|
| 3,157,524 A | | 11/1964 | Artandi |
| 4,320,201 A | | 3/1982 | Berg et al. |
| 4,412,947 A | * | 11/1983 | Cioca |
| 4,614,794 A | | 9/1986 | Easton et al. |
| 4,814,120 A | | 3/1989 | Huc et al. |
| 5,065,929 A | | 11/1991 | Schulze et al. |
| 5,206,028 A | * | 4/1993 | Li |
| 5,219,111 A | | 6/1993 | Bilotti et al. |
| 5,263,629 A | | 11/1993 | Trumbull et al. |
| 5,292,802 A | | 3/1994 | Rhee et al. |
| 5,405,073 A | | 4/1995 | Porter |
| 5,660,857 A | | 8/1997 | Haynes et al. |
| 5,673,842 A | | 10/1997 | Bittner et al. |
| 5,697,543 A | | 12/1997 | Burdorff |

FOREIGN PATENT DOCUMENTS

| | | | |
|---|---|---|---|
| DE | 3409372 A | | 9/1985 |
| EP | 033548 | | 8/1981 |
| JP | 5-92925 | * | 4/1993 |
| WO | WO 9607356 | | 3/1996 |

OTHER PUBLICATIONS

Mitchel, J.F., Azrin, M.A., Fram, D.B. McKay, R.G.,: "Novel Collagen Vascular Plug for Femoral Ateriotomy Sealing; Acute and Chronic in Vivo Studies", Journal of Interventional Cardiology, vol. 9, No. 1, Feb. 1, 1996, pp. 25–33, XP000900433.
European Search Report, Application No. EP 98308041, Date of Completion of Search: Aug. 17, 2000.
Nachf Ruhland, Derwent World Patents Index, Dialog File No. 351 Acession No. 4410723, English Abstract of DE 3409372 A1, Sep. 19, 1985; Derwent Information Ltd.

* cited by examiner

Primary Examiner—Mathieu D. Vargot
(74) Attorney, Agent, or Firm—Theodore Shatynski

(57) ABSTRACT

The invention provides biopolymer sponge tubes closed at one end for use in surgery. The preferred biopolymer iscollagen. The biopolymer sponge tubes are prepared by forming an aqueous dispersion of the biopolymer, introducing the dispersion into tube-shaped moulds, freezing the dispersion in the moulds to form a shaped, aqueous dispersion, followed by freeze-drying the frozen aqueous dispersion. The tubes are fitted over endoscopic surgical staplers to provide improved sealing of stapled tissues, especially for air-tight sealing in lung resections.

20 Claims, 4 Drawing Sheets

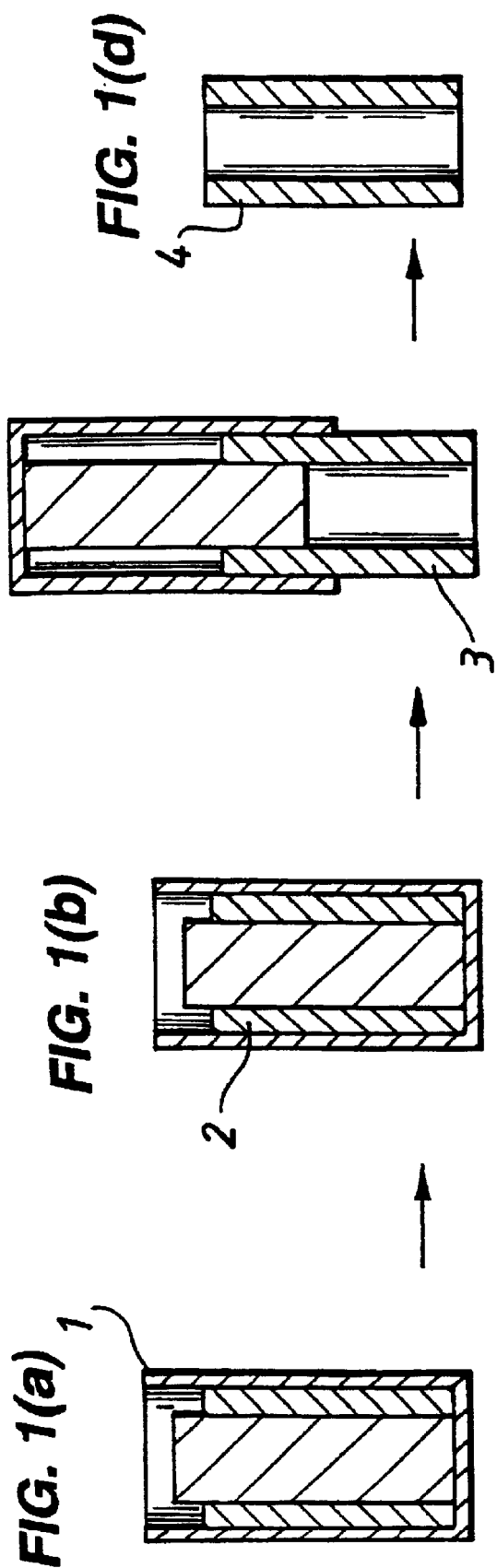

METHODS FOR MAKING BIOPOLYMER SPONGE TUBES

RELATED PATENT APPLICATIONS

This patent application is a divisional patent application of U.S. Ser. No. 09/164,793, filed Oct. 1, 1998.

FIELD OF THE INVENTION

The present invention relates to biopolymer sponge tubes and the use thereof in surgery.

BACKGROUND OF THE INVENTION

Surgical staple guns are widely used in the haemostasis and subsequent sealing of tissue following surgical procedures. For example, in the sealing of tissue following lung volume reductions for patients with emphysema.

Typically, the linear surgical staplers have two separate barrels of differing dimensions, namely a staple cartridge and an anvil, which close together during the stapling. The Burdorff, U.S. Pat. No. 5,697,543 issued Dec. 16, 1997, the Bittner et al., U.S. Pat. No. 5,673,842 issued Oct. 7, 1997, and the Schulze et al., U.S. Pat. No. 5,065,929 issued Nov. 19, 1991, each of which are incorporated herein by reference, provide examples of surgical staplers.

Often surgical staplers are indicated for use with a buttressing material, such as bovine pericardium, which surgeons use to reinforce staple lines and prevent leaks. According to current surgical procedure, the pericardium is wrapped around the barrels of the stapler prior to use. In use, the two barrels of the staple gun are placed on either side of the tissue that requires sealing. The stapling action brings together the two barrels with the pericardium, which is stapled into position at the appropriate site. The pericardium then acts as a seal to prevent exudate/air leakage.

The use of bovine pericardium in the above stapling procedure suffers from the drawbacks of possible antigenicity of the bovine pericardium, and lack of control over the precise shape, configuration and thickness of the bovine pericardium.

It is known to use pledgets of material to achieve hemostasis along a staple line as shown in the Trumbell et al., U.S. Pat. No. 5,263,629, issued Nov. 23, 1998 and incorporated herein be reference. Trumbell et al. provide rectangular pledgets of a fabric-like material, preferably having hemostatic properties, between the anvil and the staple cartridge in a surgical stapler. Staples are fired through both the pledget and the tissue to adhere the pledget to the tissue along the staple line. Placement and retention of the pledgets in the stapler can be quite tricky.

It is known to provide collagen tubes by the extrusion of a collagen gel into a coagulating bath. Such tubes have been used in micro-surgery, and for vascular prostheses. Implanted collagen films and/or collagen sponges have been suggested as slow-release matrices for therapeutic agents. The properties and applications of collagen biomaterials have been reviewed by A. Huc in Journal of American Leather Chemists Association, Vol. 80, pages 195–212 (1985).

U.S. Pat. No. 3,157,524 describes forming porous collagen tubes by freezing an aqueous collagen slurry in a tubular mold, followed by solvent drying in an anhydrous isopropanol bath.

Alternatively, the slurry may be frozen onto the outside of a tube through which a suitable refrigerant is passed, followed by solvent drying. The sponges are said to control bleeding in surgery through the application of pressure and coagulating material such as thrombin. No specific applications are disclosed.

It has now been found that biopolymer sponge tubes are highly suitable for replacing bovine pericardium and rectangular pledgets in the surgical stapling procedure described above.

SUMMARY OF THE INVENTION

Accordingly, the present invention provides a biopolymer sponge tube closed at one end.

The biopolymer sponge tube is closed at one end to enable it to be fitted over a barrel of a staple gun without sliding too far along the barrel.

The present invention also provides a surgical stapler comprising a staple cartridge and an anvil, and having a biopolymer sponge tube (which need not be closed at one end) fitted over the staple cartridge and/or over the anvil. Preferably, biopolymer sponge tubes are fitted over each of the staple cartridge and the anvil. Preferably, the biopolymer sponge tube or tubes are closed at one end.

The present invention further provides the use of a biopolymer sponge tube for the preparation of a surgical stapler as above for use in surgery.

The biopolymer used to make the sponge tubes may be any biocompatible and bioabsorbable polymer. Preferably, the biopolymer is selected from the group consisting of structural proteins, cellulose derivatives (including oxidised regenerated cellulose), starch derivatives, chitin, chitosan, glycosaminoglycans, and mixtures thereof. Preferred structural proteins include gelatin, all collagen types, keratin, laminin, fibrin or fibronectin. The phrase "all collagen types" encompasses type I and type II collagen, atelocollagen and other modified collagens. Suitable cellulose derivatives include carboxymethyl cellulose and hydroxyethyl cellulose, in addition to oxidised regenerated cellulose. Suitable alginates include sodium alginate, calcium alginate and mixtures thereof. Suitable glycosaminoglycans include hyaluronic acid, chondroitin sulphate, heparin and heparan sulphate.

The biopolymer sponge tube may be reinforced by a biopolymer matrix, such as a Vicryl (registered trade mark) polylactide/polyglycolide mesh. However, preferably, the biopolymer sponge is not reinforced.

Preferably, the biopolymer sponge tube consists essentially of one of more collagen types. The collagen may be chemically cross-linked to modify its physical properties and rate of resorption in vivo. Collagen is the preferred biopolymer because of its easy availability, low cost, low antigenicity, and well-understood properties, which enable the collagen sponge to be prepared with controlled physical and biological behaviour.

The biopolymer sponge tube is preferably sterile. Preferably, the biopolymer sponge tube comprises less than 10% by weight of water to enable it to be stored indefinitely without decomposition. The biopolymer sponge tube preferably further comprises a therapeutic compound selected from the group consisting of antiseptics, such as chlorhexidine, antibiotics such as streptomycin, analgesics such as ibuprofen, steroids, cell growth factors and wound healing factors. Preferably, the therapeutic compound is present in amount of 0.01% to 2% by weight, based on the weight of the biopolymer sponge tube.

Preferably, the biopolymer sponge tube is fully bioabsorbable in the mammalian body. This makes it especially suitable for use in conjunction with surgical stapling procedures, especially in endoscopic surgery. The rate of bioabsorption of the biopolymer can be controlled by cross-linking the biopolymer.

The biopolymer sponge tubes according to the present invention preferably have substantially uniform internal and external cross-sections. Preferably, the wall thickness of the tubes is also substantially constant.

Preferably, the internal and external cross-sections are both substantially circular or rectangular. Preferably, the average internal diameter of the biopolymer sponge tubes is from 3 mm to 30 mm, or preferably 5 mm to 20 mm, and the wall of the biopolymer sponge tube has a substantially uniform uncompressed wall thickness in the range of 1 to 4 mm. Preferably, the ratio of the length to the average external diameter of the biopolymer sponge tubes is in the range of 2:1 to 10:1, preferably 3:1 to 5:1. These preferred shapes and dimensions are especially suitable for fitting the biopolymer sponge tube over one or other barrel of a surgical stapler.

The biopolymer sponge tubes for use in the present invention are preferably prepared by a process comprising: providing an aqueous dispersion of the biopolymer; introducing the dispersion into a tube-shaped mold, following by freezing the dispersion to provide a shaped frozen dispersion; and freeze-drying or solvent-drying the shaped frozen dispersion to form the biopolymer sponge tube.

Preferably, the aqueous dispersion comprises 0.05–2.5% w/v of the biopolymer. The aqueous dispersion may be buffered to an optimum pH, and may also comprise therapeutic active agents for incorporation into the final biopolymer sponge tube. The aqueous dispersion may also contain emulsified lipid droplets for incorporation into the biopolymer sponge tube, as described and claimed in our patent application EP-A-0567234, and its U.S. equivalent, U.S. Pat. No. 5,660,857 issued Aug. 26, 1997 which is incorporated herein by reference, and which provide several benefits including enhancing liquid impermeability of the resulting collagen product.

A chemical cross-linking agent, such as glutaraldehyde or hexamethylene diisocyanate (HMDI) may be incorporated in the aqueous dispersion, or may be used to treat the biopolymer sponge tube following the drying step.

The tube-shaped mold is preferably in the shape of a tube closed at one end. If it is intended that the final biopolymer sponge tube should be reinforced with a bioabsorable mesh, such as a Vicryl™ (registered trade mark) polylactide-polyglycolide mesh, then the mesh is inserted into the mold with the aqueous dispersion prior to freezing.

Preferably, the frozen aqueous dispersion is removed from the mold prior to drying. This can be achieved by warming the mold slightly and inverting the mold to allow the frozen aqueous dispersion to drop from the mold. Preferably, the central part of the mold defining the inside wall of the tubular frozen aqueous dispersion can be warmed and removed from the mold automatically. More preferably, the end (i.e. base wall) of the mold is moveable in piston fashion along the length of the mold to expel the frozen aqueous dispersion from the mold.

Preferably, an array of tube-shaped molds is provided for simultaneous molding and freezing of a plurality of frozen aqueous dispersions. More preferably, the steps of pouring the aqueous dispersion into the mold, freezing, and expelling the frozen aqueous dispersion from the mold are alternated.

The shaped frozen dispersion is freeze-dried or solvent-dried to form the biopolymer sponge tube. Freeze-drying is typically carried out at −10° C. to +20° C. overnight. Solvent drying is preferably carried out in a succession of baths of anhydrous isopropyl alcohol as described in U.S. Pat. No. 3,157,524, the entire content of which is expressly incorporated herein by reference.

The dried biopolymer sponge tube is preferably packaged in aseptic packaging, and then dry sterilised, preferably by gamma-irradiation.

Specific embodiments of the present invention will now be described further, by way of example, with reference to the accompanying drawings, in which:

BRIEF DESCRIPTION OF THE DRAWINGS

FIG. 1 shows schematic cross-sectional views of stages in a process for preparing an open-ended biopolymer sponge tube;

DETAILED DESCRIPTION

Figure 2A:
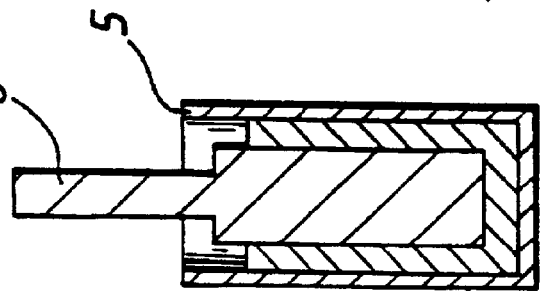
FIG. 2 shows schematic cross-sectional views of stages in a process for preparing a biopolymer sponge tube closed at one end according to the present invention.
Figure 2B:
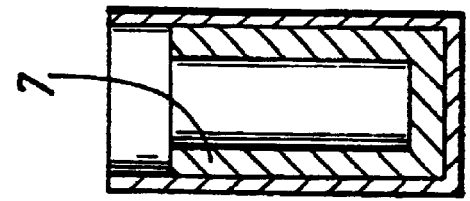
Figure 2C:
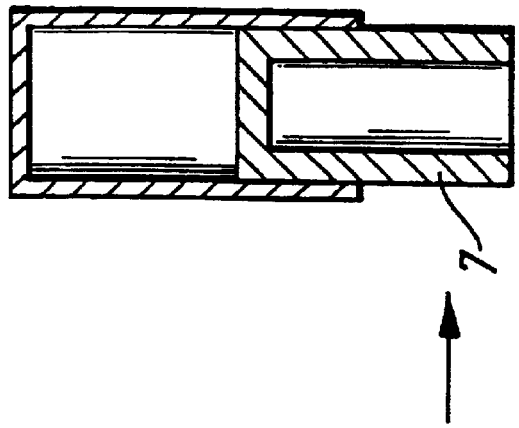
Figure 2D:
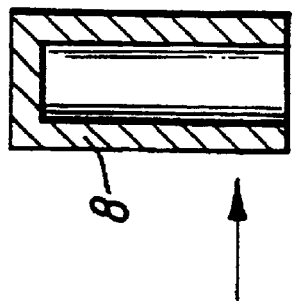
Figure 3A:
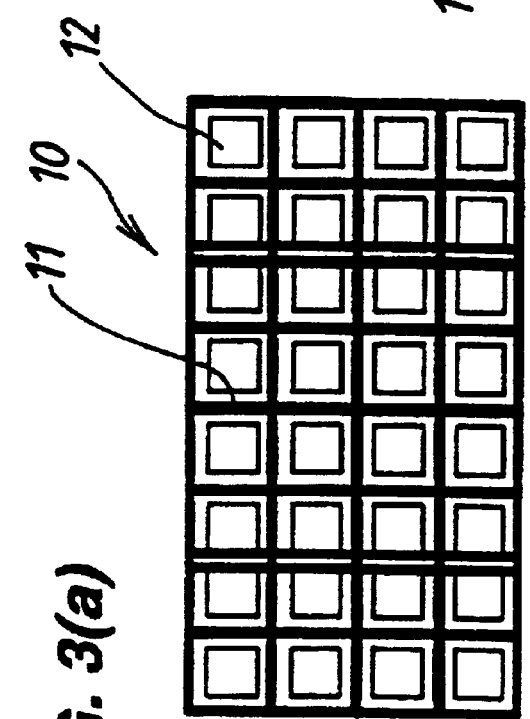
FIG. 3 shows schematic top-plan view (a) and cross-sectional views (b)–(d) of stages in a process similar to that of FIG. 2, but adapted for automated production of multiple biopolymer sponge tubes closed at one end.
Figure 3B:
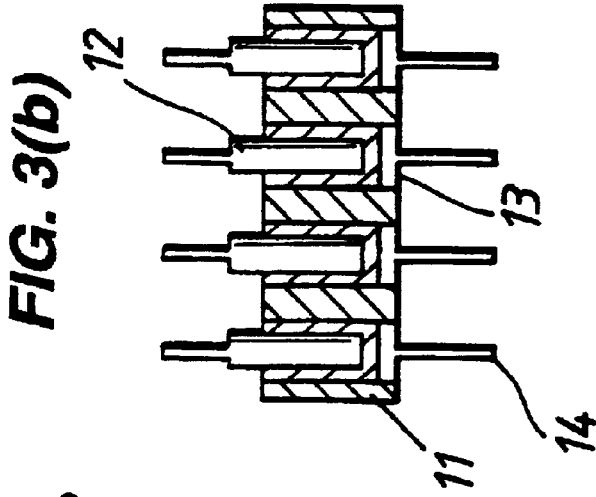
Figure 3D:
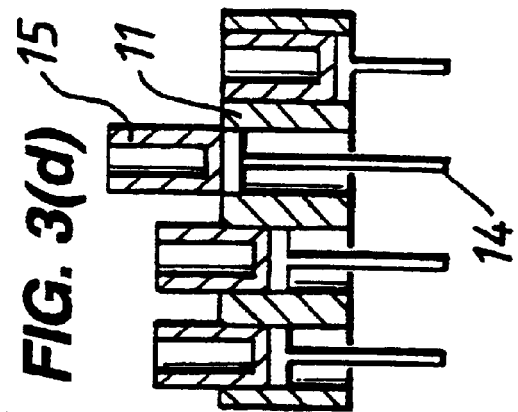
Figure 3C:
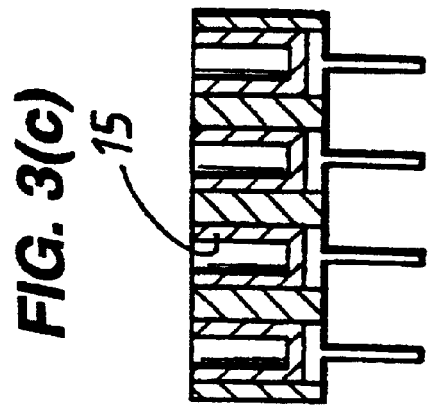
Figure 4:
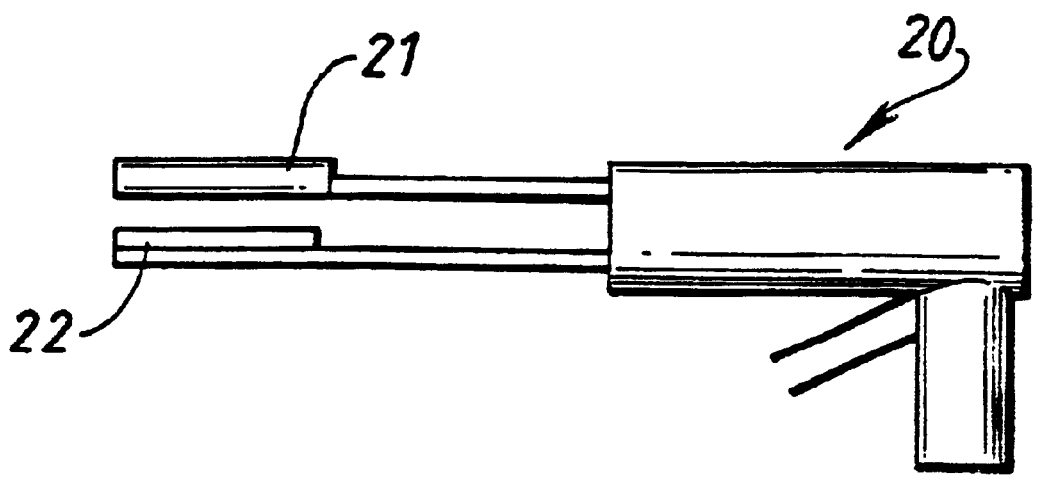
FIG. 4 shows a schematic side view of a surgical staple gun.

Procedure 1: Preparation of Open-ended Fibrous Collagen Sponge Tube

Lyophilised collagen is prepared as described in U.S. Pat. Nos. 4,614,794 or 4,320,201, the entire contents of which are expressly incorporated herein by reference. The lyophilised collagen is re-suspended in cold 0.05M acetic acid at a concentration of 1% w/v. The pH is adjusted to 3.0 with acetic acid. The resulting slurry is poured into a cylindrical mold 1 as shown in cross-section in FIG. 1(a). The mold with the slurry 2 therein is frozen at 40° C. as shown in FIG. 1(b). The frozen slurry is removed from the mold by slightly warming the mold, and inverting the mold to allow the tube to slip from the mold as shown in FIG. 1(c). The frozen tube 3 is transferred immediately to a freeze-dryer and freeze-dried to form a collagen sponge tube 4.

The resulting freeze-dried collagen tube is soft and conformable, bioabsorbable, and also exhibits useful haemostatic properties when applied with a surgical stapler.

Procedure 2: Preparation of Soluble Collagen Sponge Tube

The procedure described above in Procedure 1 is repeated, replacing the fibrous lyophilised collagen by pepsin-solubilised collagen at a concentration of 10 mg/ml. The resulting sponge tube is water soluble.

Procedure 3: Preparation of cross-linked Collagen Sponge Tube

The procedure of Procedure 1 is repeated, but with cross-linking of the collagen in the aqueous slurry. The lyophilised collagen as in Procedure 1 is resuspended in 0.05M acetic acid at a concentration of 1% w/v. The pH is adjusted to 3.0. Hexamethylene diisocyanate (HMDI) is added at 2% w/w collagen and homogenised in a Waring Blendor (3×30s). The resulting slurry is formed into collagen sponge tubes exactly as described in Procedure 1.

Procedure 4: Preparation of Gelatin Sponge Tube

The fibrous collagen slurry prepared as in Procedure 1 is gelatinised by heating to 60° C. for one hour. The slurry is then processed into a biopolymer sponge tube as in Example 1.

Procedure 5: Preparation of Collagen/ORC Sponge Tubes.

Lyophilised collagen, prepared as described in U.S. Pat. Nos. 4,614,794 or 4,320,201, is resuspended in cold 0.0SM acetic acid at a concentration of 10 mg/ml. Milled ORC powder (milled SURGICEL® oxidised regenerated cellulose cloth) is added to the suspension in a ration of 1:3 ORC:collagen and homogenised using a Waring Blendor on low speed for 3×10s. The slurry is degassed in a vacuum oven for 10 min and then poured into the appropriate mold. The mold with the slurry is then processed as described in Procedure 1.

EXAMPLE 1

Preparation of Biopolymer Sponge Tubes with Closed End

Biopolymer sponge tubes closed at one end are prepared as shown in schematic cross-section in FIG. 2. A biopolymer slurry as described in Procedures 1–6 is poured into a mold in the shape of a closed-end tube and formed from an outer shell and a central mandrel 6. The slurry and mold are frozen at −40° C. The central mandrel 6 of the mold is warmed slightly and removed from the inside of the cast open-ended tube 7. The outer shell 5 of the mold is then inverted and warmed slightly to release the frozen slurry in the shape of a tube closed at one end 7. The cast, frozen tube is then immediately freeze-dried to give a biopolymer sponge tube closed at one end 8.

EXAMPLE 2

Multiple Molding of Biopolymer Sponge Tubes

FIG. 3 shows an apparatus 10 for the multiple, automated production of biopolymer sponge tubes closed at one end. The apparatus comprises an array of wells 11 defining the outer parts of the molds, and a complementary array of mold mandrels 12 for insertion into the wells. The floor 13 of each mold well is mounted on a piston 14, and is slideably moveable inside the well 11 to push the frozen, cast tubes 15 out of the wells following the casting and freezing steps. The frozen tubes 15 are collected and freeze-dried.

EXAMPLE 3

Use of Biopolymer Sponge Tubes on Surgical Stapler

Figure 5:
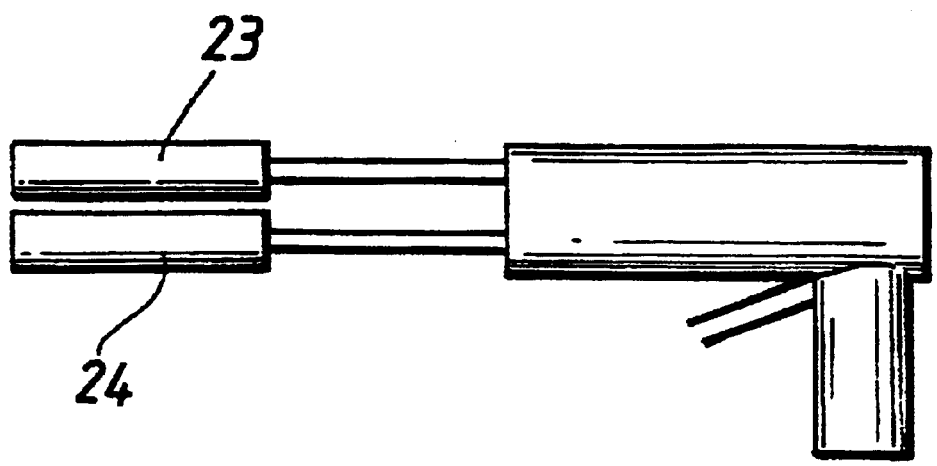
FIG. 5 shows the staple gun of FIG. 4 fitted with biopolymer sponge tubes according to the invention.

FIG. 3 shows a schematic view of a surgical staple gun 20 for use in lung volume reduction surgery. The staple gun is provided with a stapler cartridge barrel 21 and an anvil barrel 22. In use, biopolymer sponges tube 23,24 having a closed end are slipped over the end of each of the cartridge barrel 21 and the anvil barrel 22 as shown in FIG. 5.

The two barrels 21,22 of the staple gun 20, with the biopolymer sponge tubes 23,24 in place, are then placed on either side of the tissue that requires sealing. The stapling action brings together with two barrels whilst the tubes, which flatten during the stapling procedure, are stapled into position at the appropriate site. The flattened biopolymer tubes then act as a seal to prevent exudate/air leakage, and where appropriate to encourage haemostasis.

Use of surgical staples in lung resection is known to those of skill in the art. Such procedure is enhanced when biopolymer sponge tubes according to the present invention are used with the stapler in effecting the lung resection.

The above embodiments have been described by way of example only. Many other embodiments falling within the scope of the accompanying claims will be apparent to the skilled reader.

What is claimed is:

1. A method for producing biopolymer sponges comprising the steps of:
    (a) providing an aqueous dispersion of the biopolymer;
    (b) introducing the dispersion into a mold;
    (c) freezing the dispersion to provide a shaped frozen dispersion;
    (d) heating the mold and releasing the shaped frozen dispersion from the mold; and
    (e) drying the released frozen dispersion.

2. The method of claim 1, wherein the mold is a mold for making tubes.

3. A method for producing biopolymer sponges comprising the steps of:
    (a) providing an aqueous dispersion of the biopolymer;
    (b) introducing the dispersion into a mold for making tubes;
    (c) freezing the dispersion to provide a shaved frozen dispersion;
    (d) heating the mold and releasing the shaved frozen dispersion from the mold; and
    (e) drying the released frozen dispersion;
wherein the mold comprises an outer cylindrical shell having a distal closed end and proximal opened end a central block being disposed within the shell and resting on the distal closed end of the shell, whereby the block and shell form an annular space therebetween.

4. The method of claim 3, wherein the heating step (d) involves heating the central block.

5. The method of claim 3, wherein the heating step (d) involves heating the outer cylindrical shell.

6. The method of claim 2, wherein the mold comprises an outer cylindrical shell having a distal closed end and a proximal opened end, a mandrel for insertion into the shell, whereby the shell and the mandrel define an annular space along the longitudinal dimension of the shell and mandrel and define an open area between the base of the mandrel and the distal closed end of the shell, the open area contiguous with the annular space when the mandrel is placed in the shell.

7. The method of claim 6, wherein the heating step (d) involves heating the mandrel.

8. The method of claim 6, wherein the heating step (d) involves heating the outer cylindrical shell.

9. The method of claim 2, wherein the mold comprises a cylindrical outer shell opened at both the distal and proximal ends, a mandrel, and a piston, whereby the shell and the mandrel define an annular space along the longitudinal dimensions of the shell and mandrel, the piston insertable into and though the distal end of the shell, the piston and base of the mandrel defining an open space therebetween, the open space being contiguous with the annular space between the mandrel and shell.

10. The method of claim 9, wherein the heating step (d) involves heating the mandrel.

11. The method of claim 9, wherein the heating step (d) involves heating the shell.

12. The method of claim 9, wherein the heating step (d) involves heating the piston.

13. The method of claim 2, wherein the mold comprises an array of wells defining the outer parts of the mold, a complimentary array of mold mandrels for insertion into the wells, wherein the floor of each mold well is mounted on a piston which is slideably moveable inside the well to push the frozen dispersion out of the wells.

14. The method of claim 13, wherein the heating step (d) involves heating the mandrels.

15. The method of claim 13, wherein the beating step (d) involves heating the array of wells.

16. The method of claim 13, wherein the heating step (d) involves heating the pistons.

17. The method of claim 1, wherein the drying step (e) is freeze-drying.

18. The method of claim 17, wherein the mold is a mold for making tubes.

19. The method of claim 1, wherein the drying step (e) is solvent-drying.

20. The method of claim 19, wherein the mold is a mold for making tubes.

* * * * *